United States Patent
Harden et al.

(10) Patent No.: US 6,716,453 B1
(45) Date of Patent: Apr. 6, 2004

(54) METHOD FOR INCREASING THE ACTIVE LOADING OF COMPRESSIBLE COMPOSITION FORMS

(75) Inventors: Jerome W. Harden, Philadelphia, PA (US); Duane Glover, Philadelphia, PA (US); Bruce K. Redding, Jr., Broomall, PA (US)

(73) Assignee: Verion, Inc., Lionville, PA (US)

( * ) Notice: Subject to any disclaimer, the term of this patent is extended or adjusted under 35 U.S.C. 154(b) by 0 days.

(21) Appl. No.: 09/576,356

(22) Filed: May 22, 2000

(Under 37 CFR 1.47)

Related U.S. Application Data

(60) Provisional application No. 60/134,977, filed on May 20, 1999.

(51) Int. Cl.[7] .............................. A61K 9/20; A61K 9/14; A61K 9/26; A61K 47/00; A61K 9/16
(52) U.S. Cl. ..................... 424/464; 424/465; 424/466; 424/470; 424/439; 424/441; 424/442; 424/489
(58) Field of Search .................... 424/464, 465, 424/466, 439, 441, 442, 470, 489

(56) References Cited

U.S. PATENT DOCUMENTS

| | | | |
|---|---|---|---|
| 3,584,114 A | 6/1971 | Cavalli et al. ................ 424/38 |
| 3,725,556 A | 4/1973 | Hanssen et al. ............. 424/357 |
| 3,873,694 A * | 3/1975 | Kanig ......................... 424/127 |
| 4,072,535 A * | 2/1978 | Short et al. .................. 106/210 |
| 4,251,518 A * | 2/1981 | Moore et al. ................ 424/180 |
| 4,356,198 A * | 10/1982 | Parada et al. .................. 426/96 |
| 4,439,453 A | 3/1984 | Vogel .......................... 514/629 |
| 4,950,484 A * | 8/1990 | Olthoff et al. .............. 424/464 |
| 5,137,730 A | 8/1992 | Dennis et al. .............. 424/465 |
| 5,455,342 A * | 10/1995 | Redding, Jr. ................ 536/102 |
| 6,391,335 B1 * | 5/2002 | Pather et al. ................ 424/466 |

OTHER PUBLICATIONS

Starch 1500 Technical Data, Colorcon, Feb. 1999.

*Binder Evaluation of Fine Particle Size Hydroxypropylcellulose for Roller Compaction Technology*, Pharmaceutical Technology Report, Hercules Incorporated, G. W. Skinner, AAPS Annual Meeting, San Francisco, Nov. 6, 1998.

* cited by examiner

*Primary Examiner*—James M. Spear
*Assistant Examiner*—S. Tran
(74) *Attorney, Agent, or Firm*—Synnestvedt & Lechner LLP

(57) ABSTRACT

A process for increasing the percentage of active ingredient relative to non-active excipient in a compressible formulation, and also for reducing tablet size, by excluding an amount of the excipient and including in its place a reduced amount of a polysaccharide material.

29 Claims, No Drawings

METHOD FOR INCREASING THE ACTIVE LOADING OF COMPRESSIBLE COMPOSITION FORMS

This application claims the Benefit of Provisional Application No. 60/134,977 filed May 20, 1999.

FIELD OF THE INVENTION

The present invention relates to improvements in composition formulation technology, more particularly improvements in the formulation of compressible compositions including one or more active ingredients that are combined with inactive excipients such as binders and/or hardening agents to enable the production of a final compressed form such as a tablet, pellet, bead or the like.

BACKGROUND OF THE INVENTION

The compressed tablet is one of the oldest and most popular unit forms for oral dosage of medicinal substances. As a result of the introduction of new carriers and compression vehicles, tablets are replacing many forms of pills, powders and capsules. Accordingly, tablets presently represent the largest production volume of all pharmaceuticals and nutritional supplements.

The reasons for the widespread use of tablets are apparent, since tablets facilitate: (1) administration of medication in an accurate dose; (2) fast and accurate dispensing with less chance of error and contamination: (3) ease of administration: (4) administration in a form in which the time and area of contact between the active ingredient and the taste buds are reduced, thus obviating the physiological problems associated with the oral administration of drugs that possess a bitter taste and, in the case of coated tablets, with drugs that possess a disagreeable odor; (5) release of drugs at specific locations in the gastro-intestinal tract to prevent degradation of drugs sensitive to the low pH environment in the stomach, prevent release of drugs that irritate the gastric mucosa in the stomach, and facilitate local action or preferential absorption at specific sites in the tract: (6) enhanced stability by effecting a marked reduction in the surface of the drug exposed to the environment; (7) rapid production; and (8) economy and ease in storage, packaging and shipping.

The preparation of a solid compressed form containing one or more active ingredients (such as drugs or nutrients such as vitamins) requires that the materials to be compressed into the form possess certain physical characteristics that lend themselves to such processing. Among other things, the material to be compressed must be free flowing, must be lubricated, and, importantly, must possess sufficient cohesiveness to insure that the solid dosage form remains intact after compression.

A tablet is formed typically by pressure being applied to the material to be tableted on a tablet press. A tablet press includes a lower punch which fits into a die from the bottom and a upper punch having a corresponding shape and dimension which enters the die cavity from the top after the tableting material fills the die cavity. The tablet is formed by pressure applied on the lower and upper punches. The ability of the material to flow freely into the die is important in order to insure that there is a uniform filling of the die and a continuous movement of the material from the source of the material, e.g. a feeder hopper. The lubricity of the material is crucial in the preparation of the solid dosage forms since the compressed material must be readily ejected from the punch faces.

Since most drugs and nutritional supplements have none or only some of these properties, methods of tablet formulating have been developed to impart these desirable characteristics to the material(s) which is to be compressed into a solid dosage form. Typically, excipients, which impart good flow and compression characteristics to the material as a whole, are added to the active material that is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

There are three general methods of preparing the materials to be included in the solid dosage form prior to compression: (1) dry granulation; (2) wet granulation; and (3) direct compression.

Dry granulation procedures may be utilized where one of the constituents, either the drug or the diluent, has sufficient cohesive properties to be tableted. The method includes mixing the ingredients with a lubricant, if required, slugging the ingredients, dry screening, lubricating and finally compressing the ingredients.

The wet granulation procedure includes mixing the powders to be incorporated into the dosage form and thereafter adding solutions of a binding agent to the mixed powders to obtain a granulation. Thereafter, the damp mass is screened, e.g., in a 6- or 8-mesh screen and then dried, e.g., via tray drying or fluid-bed drying. One disadvantage of the wet granulating technique is that it has been known to reduce the compressibility of some pharmaceutical ingredients including microcrystalline cellulose.

Direct compression is a relatively quick process wherein the powdered materials included in the solid dosage form are compressed directly without modifying their physical nature. Usually, the active ingredient, direct compression vehicle and other ancillary substances, such as a glidant to improve the rate of flow of the tablet granulation and lubricant to prevent adhesion of the tablet material to the surface of the dies and punches of the tablet press, are blended in a twin shell blender or similar low shear apparatus before being compressed into tablets.

Direct compression is usually limited to those situations where the drug or active ingredient has a requisite crystalline structure and the physical characteristics required for formation of an acceptable tablet. However, only a very limited number of substances possess enough cohesive strength and flowability to allow direct compression without previous granulation. A limited number of crystalline materials, such as potassium bromide and potassium chloride, can be compressed without preliminary treatment. Also, drugs such as aspirin and phenolphthalein can be directly compressed after blending with suitable tableting excipients.

It has been estimated that about 20 percent of the materials used for tableting in the pharmaceutical field may be compressed directly. In order to use this method to a greater extent, many more materials are modified either by treating the material in some special way during early stages of preparation, or by adding a direct compression vehicle, i.e., a dry binder or excipient material which will mix with the active ingredient to provide a flowable powder and form an easily compressible carrier.

There are currently several available binders or excipients that can be used as direct compression vehicles. They include spray-dried lactose; anhydrous lactose: microcrystalline cellulose; dicalcium phosphate dihydrate, unmilled; spray-congealed mannitol; ungelatinized starch (e.g., cornstarch), and partially or fully pregelatinized starch.

Microcrystalline cellulose, processed cellulose, has been utilized extensively in the pharmaceutical industry as a direct compression vehicle for solid dosage forms. Microcrystalline cellulose is commercially available under the tradename Emcocel® from Edward Mendell Co., Inc. and as Avicel® from FMC Corp. Compared to other directly compressible excipients, microcrystalline cellulose is generally considered to exhibit superior compressibility and disintegration properties as long as it is not wet granulated prior to compression.

Many types of partially or fully pregelatinized starches are commercially available for use in direct compression tablet formulations. Pregelatinized cornstarch provides tablets with hardness properties in the range of 1 to 4 Kp. Present demands, however, require hardness levels in the range of 10–14 Kp and higher, an expectation which many starches modified by prior art methods simply can not meet. While the use of starch in tableting formulations is still common practice, problems of uniformity between modified batches and a demand for tablets of greater hardness resulted in its departure from the status of a preferred pharmaceutical excipient.

The prior art also discloses inherently cost ineffective chemically modified starches requiring the additional expense of crosslinking chemicals or functional reagents to produce the desired physical characteristics in the substrate. Disposal problems associated with unwanted reaction by-products further adds to cost and environmental concerns. Also, chemical modification methods yield product in batch quantities, rather than on a continuous or semi-continuous basis and, therefore, are less time efficient. Production rates are further diminished when more than one chemical modification must be made to the starch substrate to yield a product with all of the desired characteristics. Moreover, the starch end product itself often suffers from other limitations similar to the deficient tablet hardness profiles, discussed above. Inferior viscosity, shear resistance and thermal profiles of the starch end product, for example, may frustrate the performance of products incorporating starch modified by prior art means.

Since each excipient added to a formulation necessarily increases the tablet size of the final product, compression techniques are often limited to formulations containing a rather low load of active ingredient per compressed tablet. Solid dosage forms containing the active ingredient to be administered in a relatively high load or dose (e.g., the drug itself comprises a substantial portion of the total compressed tablet weight), could only be directly compressed if the drug itself had sufficient physical characteristics (e.g., cohesiveness) for the ingredients to be directly compressed.

For example, acetaminophen, a widely used analgesic, is considered to be a high load active ingredient. Most commercial compressed tablet formulations include anywhere from 70 to 85% by weight acetaminophen per finished tablet. This high load of active ingredient combined with its rather poor physical characteristics for direct compression has not allowed pharmaceutical manufacturers to use direct compression techniques to prepare the final tablets.

Thus, another limitation of direct compression as a method of tablet manufacturing is the potential size of the compressed tablet. If the amount of active ingredient is high, a pharmaceutical formulator may choose to wet granulate the active with other excipients to attain an acceptably sized tablet with the desired amount of active ingredient, such as acetaminophen. Usually the amount of filler/binder or excipients needed in wet granulation is less than that required for direct compression since the process of wet granulation contributes to some extent toward the desired physical properties of a tablet. Even so, other reasons, such as for example the loss of compressibility associated with the wet granulation of MCC, prevent wet granulation from always being the solution to increase active loading and reduce the size of a compressed tablet.

Reported Developments

Exemplary United States patents relating to directly compressible tablets include U.S. Pat. No. 3,584,114 to Cavalli, et al., U.S. Pat. No. 3,725,556 to Hanssen, et al., U.S. Pat. No. 3,873,694 to Kanig, U.S. Pat. No. 4,072,535 to Short, and U.S. Pat. No. 4,439,453 to Vogel.

U.S. Pat. No. 5,455,342 discloses starch and other polymers treated with high pressure using a piston apparatus resulting in a starch end-product that manifests several changes in physical properties, including: an altered thermal profile (the onset of melting and the actual melting point is raised, the heat energy required to effect melting is also altered); altered disintegration and solubility properties (the solubility rate in water and other solutions in an ambient or heated environment is slowed by as much as 300%); an altered viscosity profile (pressure treated starch exhibits a higher viscosity for a longer period of time); an altered tableting profile (the treatment of waxy maize pregelatinized starches results in a starch which forms harder tablets at lower than conventional compression forces); and an altered turbidity profile (the clarity of solutions made with pressure treated starch is improved).

U.S. Pat. No. 5,455,342 discloses also that pressure treated starch samples are useful as excipients in tableting processes in view of the need for a more readily dissolvable excipient than microcrystalline cellulose. The '342 patent discloses the direct compression preparation of pharmaceutical tablet compositions including acetaminophen and vitamin C where microcrystalline cellulose (MCC) and untreated starch are replaced with equal amounts of the pressure treated starch. Resulting tablets exhibit acceptable friability, high hardness, and slower dissolution rates than the MCC containing compositions.

U.S. Pat. No. 4,950,484 discloses antibiotic compositions that are wet granulated and compressed and are characterized as including a high percentage of active antibiotic which can be 20–70 wt %, but is preferably 50–65 wt %. These compositions contain a substantial amount of MCC or microfine cellulose in combination with a disintegrant. The '484 patent disclose also that 20–50 wt %, preferably 35–45 wt % based on the weight of antibiotic of microcrystalline and/or microfine cellulose is used in the granulate, while further amounts, 4–20 wt %, preferably 8–15 wt % based on the weight of the antibiotic, of microcrystalline and/or microfine cellulose are then added to the granulate. These compositions also include 2–20 wt %, preferably 7–10 wt %, based on the weight of the antibiotic of a low-substituted hydroxypropylcellulose as a disintegrant.

U.S. Pat. No. 5,137,730 discloses an improved tablet composition for drugs or active ingredients prone to poor tableting properties. Although the '730 patent discloses that the premixture used in wet granulation consists essentially of between about 85 and 99.9 percent by weight of the active ingredient and between about 0.1 and 15 percent by weight of citric acid, and one or more other formulation ingredients added to the premixture, the final compressed includes substantially more excipients in the product.

Thus, there still remains a need in the industry for techniques and formulation excipients which would allow artisans to prepare wet granulation and direct compression dosage forms containing relatively high amounts by weight of active ingredient(s) such as for example acetaminophen and vitamin formulations.

Verion Inc. of Lionville, Pa., formerly known as Delta Food Group, Inc. of Aston, Pa., sells the commercially available product, Del Tab™ excipient which is manufactured in accordance with the teachings of U.S. Pat. No. 5,455,342. This product, previously made available under the mark, Delta Starch®, possesses superior properties to microcrystalline cellulose and standard starches used in pharmaceutical and nutritional supplement formulations. The Delta Starch product literature describes that Delta Starch (otherwise identified as DS-901), versions A and C, produce very hard tablets at low compression pressures. For example, a 200 mg tablet made of pure DS-901, pressed at just 1 ton, will possess an average hardness of 20 Kp, and that ideal applications include chewable tablets where mouth feel, tablet strength, yet good friability are required. DS-901-C is described as ideal for direct compression where its performance is comparable to microcrystalline cellulose in most tableting operations. As a wet binder DS-901-C is described as superior to all other conventional pharmaceutical grade starch binders and is also superior to Microcrystalline Cellulose (MCC), requiring less time and less moisture to provide it's binding function, while also enabling a significant tablet hardness, with friability comparable to Starch 1500 or MCC variations. DS-901-C is described as functioning as an anti-caking agent when used in loading levels from 10 to 35% but also provides a higher tablet hardness than other starches. The product literature describes the following examples of tablets produced with DS 901-C: Formulation VIT-101 used DS-901-C as the diluent and wet binder with Vitamin C. Compared to Starch 1500, DS-901-C used far less moisture and reduced the wet granulation time by half, yet retained tablet hardness, friability and appearance. Formulation VIT-102 used DS-901-C as a direct compression diluent for an extremely hygroscopic compound, choline chloride crystal. DS-901-C provides longer shelf life and greater stability over MCC in this application.

Delta Starch product literature also describes DS901-B as used as a wet binder for pharmaceutical tableting, and is particularly used as a flow control binder for such products as acetaminophen and ascorbic acid formulations which may use from 10 to 35% starch as a binder in fluid bed granulation processing. DS901-B provides excellent binding, while using as much as 30% less water during fluidizing processing, and enabling as much as 50% shorter overall processing times in a wet granulation or fluid bed processing procedure. Additionally the DS 901-B ingredient after wet granulation provides improved compressive strength, higher tablet hardness, and a reduction in the need for critical diluents such as microcrystalline cellulose or lactose, while providing strong tablets with reduced capping and friability. Nonetheless, the product literature does not recognize or suggest that the Delta Starch product could eliminate substantially all of the diluent, binders and hardening agents required in prior art tableting formulations and significantly reduce tablet size while retaining desired tablet properties.

The present invention is based on the surprising discovery that small amounts of polysaccharide tableting excipients previously included in formulations at higher than 10% by weight, including abrupt pressure treated polymeric materials, such as pressure treated starch or dextrin, not only function simply as a binder or hardening agent similar to microcrystalline cellulose, but also possess properties that permit the formulator to eliminate unexpectedly high levels of such excipients in compressible compositions. The present discovery enables the compression manufacture of reduced size tablets and high active loading tablets which otherwise would be difficult and/or expensive to prepare with the standard required amounts of excipients.

SUMMARY OF THE INVENTION

The present invention relates to a process for increasing the percentage of active ingredient relative to non-active excipient in a compressible formulation by taking the following steps:
  i) determining the formula of a compression formulation including one or more active ingredients and a first amount of one or more non-active hardening or binder excipient or both;
  ii) preparing a revised formulation excluding said first amount of excipient and including a polysaccharide material in a second amount of about 50 to about 1 percent by weight of said first amount;
  iii) mixing said active ingredients and said polysaccharide material to form a reduced volume mixture; and
  iv) compressing the reduced volume mixture to form a high active loaded composition.

The process may be used to form the reduced volume mixture into an object such as a tablet, a pellet, sphere, disk or any shape susceptible to compression formation, such as in tablet stamping or extrusion pelleting. The resulting product is particularly useful as a food, a nutritional supplement or a pharmaceutical composition suitable for animal or human ingestion.

Another aspect of the present invention relates to a process for reducing the size of a first tablet formed by compressing a mixture of active ingredient and an excipient having acceptable hardness and friability and disintegration time, comprising the steps of:
  i) mixing said active ingredient with a polysaccharide material, and
  ii) compressing the mixture of said ingredient and said polysaccharide material to form a reduced size second tablet,
  iii) wherein said excipient consists essentially of one or more hardening agent and binder other than said polysaccharide material, and
  iv) wherein said reduced size second tablet excludes about 30 to about 99 percent of said excipient and exhibits an acceptable hardness, friability and disintegration time.

Depending on the compressibility of the active ingredients in the formulation, the ratio of active ingredients to inactive excipients can be increased significantly. Advantages of the present invention include reduced costs of production, improvements in direct compression and wet granulation processing, reduction in patient dosing, reduced tablet size to facilitate dosage acceptability and reduction in choking hazards.

Reduced size tablets produced by the present invention may be manufactured for human or animal consumption and exhibit a hardness and friability within acceptable consumption ranges.

DETAILED DESCRIPTION

The following terms shall have the meanings as described below:

"Binders" are agents that impart cohesive qualities to the powdered material(s). Commonly used binders include acacia, alginic acid, alkali metal alginate, carbomer, carboxymethylcellulose sodium, dextrin, dicalcium phosphate dihydrate, ethyl cellulose, gelatin, glucose, guar gum, hydroxyethyl-, hydroxypropyl- and hydroxypropyl methylcellulose, hydrogenated vegetable oil, spray-dried lactose; anhydrous lactose, magnesium aluminum silicate, maltodextrin, methylcellulose, microcrystalline cellulose, unmilled; spray-congealed mannitol; povidine, starch (e.g., corn starch), partially or fully pregelatinized starch, and zein.

"Compressible" means a mixture of particles that is capable of forming a tablet after compression and does not remain in a powdered or substantially powdered form or mixture of agglomerated fragments.

"Dextrin" means a mixture of polysacharrides having an empirical formula, $(C_6H_{10}O_5)_n \cdot xH_2O$ derived from the heat degradation or partial hydrolysis of starch. To be categorized as a Dextrin, the US Pharmacopeia publishes limit specifications including a a bulk density less than 0.8 g/cm3, a tap density of less than 0.91 g/cm3 and a particle size distribution where about 100% of the particles are less than 60 microns. Dextrins may be produced in a dry reaction, pyrolysis, in the presence of acid or result from the degradation of any aqueous slurry or solution of the starch subjected to high pressure treatment in accordance with the process described in U.S. Pat. No. 5,455,342.

"Diluent" is frequently added in order to increase the bulk weight of the material to be tableted in order to make the tablet a practical size for compression. This is often necessary where the dose of the drug is relatively small.

"Disintegrant" is often included in order to ensure that the ultimately prepared compressed solid dosage form has an acceptable disintegration rate in an environment of use (such as the gastrointestinal tract). Typical disintegrants include starch derivatives and salts of carboxymethylcellulose.

"Friability" is related to the integrity of the tablet and is represented as the percentage of tablet weight loss occurring after a certain number of revolutions in a Vanderkamp Friabilator. The highest integrity tablet has the lowest percentage friability.

"Hardening agent" means an excipient that is incorporated into a compressed tablet composition to impart increased hardness thereto. Exemplary hardening agents include calcium carbonate, di- and tri-calcium phosphate, calcium sulfate, microcrystalline cellulose, powdered cellulose, dextrates, dextrin, sugars such as dextrose, fructose, lactose, mannitol, sorbitol, sucrose, glyceryl palmitostearate, kaolin, magnesium carbonate, magnesium oxide, maltodextrin, potassium chloride, sodium chloride, starch, pregelatinized starch, talc and hydrogenated vegetable oil.

"Hardness" of the tablet is the force in kp (kilopond) or SCU (1 SCU=1.4 kp) required to break a tablet. The strongest tablet has the highest kp value.

"Lubricants" are typically added to prevent the material(s) being tableted from sticking to the tablet press punches. Commonly used lubricants include magnesium stearate, stearic acid and calcium stearate.

"Maltodextrin" is a mixture of polysaccharides resulting from acid or enzyme hydrolysis of common corn starch or waxy maize starch. The mixture consists principally of D-glucose units linked primarily by alpha 1–4 bonds and is characterized by a relatively uniform distribution of polymeric polysaccharide species.

"Polysaccharide material" as used herein means an organic polymeric material considered as derived from aldose or ketoses by condensation polymerization, composed of repeating monosaccharide units, and are branched or straight-chained, looped or coiled. An exemplary polysaccharide derived from hexoses has the general formula $(C6H10O5)_n$. Polysaccharide materials as meant herein include those materials that are, or may in the future be, approved for human consumption as published by the US Food and Drug Administration. Preferred polymeric materials include the dextrins and maltodextrins, as well as the polysaccharide materials identified in U.S. Pat. No. 5,455,342, hereby incorporated by reference.

"Pregelatinized starch" is defined by the National Formulary XVI as "starch that has been chemically and/or mechanically processed to rupture all or part of the granules in the presence of water and subsequently dried. Some types of pregelatinized starch may be modified to render them compressible and flowable in character."

"Starch" means a natural polymer $(C_6H_{10}O_5)_n$ derived from plant materials, and is commonly found in the form of tiny microscopic granules (5–25 microns in diameter) comprised of stratified layers of starch molecules formed around a hilum nucleus. The starch granule may be round, oval or angular in shape, and consists of a radially oriented crystalline aggregate of two anhydrous D-glucose polymers: amylose and amylopectin. The former is a straight chain polymer of several hundred glucose units linked by alpha-1–4-glycosidic linkages. Amylopectin is a branched polymer of several thousand glucose units with alpha-1–6-glycosidic linkages at the branched points and alpha-1–4 linkages in the linear regions. Individual branches may have between 20–30 glucose residues. The National Formulary XVI defines Starch as "consist[ing] of the granules separated from the mature grain of corn {*Zea mays* Linne (Fam.Gramineae)} or of wheat {*Triticum asetivum* Linne (Fam.Gramineae)}, or from tubers of the potato {*Solanum tuberosum* Linne (Fam.Solanaceae)}."

"Tablet" as used herein is intended to encompass compressed nutritive and pharmaceutical dosage formulations of all shapes and sizes, whether coated or uncoated. Substances that may be used for coating include hydroxypropylmethylcellulose, hydroxypropylcellulose, titanium oxide, talc, sweeteners and colorants.

"Abrupt pressure treated" materials useful in the practice of the present invention are preferably the pressure treated polysaccharide materials described generally in U.S. Pat. No. 5,455,342, hereby incorporated by reference. In this pressure process, a liquid substrate composition comprising the material and characterized as either a solution, slurry, dispersion, emulsion, mixture, suspension, or other substance exhibiting fluid dynamics, is treated by an apparatus wherein a shock wave transmitting extreme heat and force is applied to the substrate thereby resulting in its modification. The preferred apparatus utilizes a piston that impacts the liquid substrate with forces ranging from about 13,000 psi to 300,000 psi thereby modifying the physical properties of the material. The preferred pressure range is from about 66,000 psi to 120,000 psi, with the most preferred pressure range of about 90,000 to about 100,000 psi.

Exemplary hardening agents and binders that may be replaced by the size reduction materials of the present invention are silica, cellulose, microcrystalline cellulose, calcium carbonate, mono-, di- or tri-calcium phosphate, spray-dried lactose, anhydrous lactose, dicalcium phosphate dihydrate, unmilled, spray-congealed mannitol, ungelatinized starch (e.g., corn starch), and partially or fully pregelatinized starch.

A preferred process according to the present invention replaces at least one hardening or binder excipient consisting essentially of microcrystalline cellulose.

The preferred polysaccharide materials useful in the practice of the present invention include the dextrins and maltodextrins capable of replacing the bulk of standard tableting excipients in a direct compression tableting mixture and of imparting to a compressed tablet, incorporating said preferred polysaccharide in an amount from 1 to about 10 percent by weight, a tablet hardness from 7 kp to about 40 kp, and acceptable friability and an aqueous disintegration time of greater than about 30 seconds and less than 30 minutes in accordance with USP 701.

The most preferred polysaccharide materials useful in the practice of the present invention include abrupt-pressure treated starches, some of which may be characterized as dextrins. A special embodiment of this material comprises a starch treated with the apparatus disclosed in the '342 patent at a pressure of about 90,000 psi for about 0.1 sec. This product is sold commercially as DEL TAB™ excipient (Drug Master File Number: DMF 10572, November 1993). Other excipients that are also useful in the practice of the present invention include Delta Cellulose™ excipient, and the various pressure treated polysaccharide materials disclosed in U.S. Pat. No. 5,455,342.

It is understood that certain active ingredients are easily compressible and require little if any binder or hardening agent. Examples of such ingredients may include acyclclovir, aspirin and dextromethorphan.

For those active ingredients that are moderately compressible, examples of which include flurbiprofin, citric acid and chlorpheniramine maleate, the present process offers the unexpected benefits of providing high active loading compositions including such ingredients using either direct compression or wet granulation processing. For these moderately compressible ingredients, the resulting tablet composition may include from about 1 to about 4 percent of polymeric material and most preferably about 1 to about 4 percent of abrupt pressure treated excipient.

For those active ingredients that are moderately uncompressible, examples of which include vitamins, such as vitamin D, calcium citrate malate, the present process offers the unexpected benefits of providing high active loading compositions including such ingredients using either direct compression or wet granulation processing. For these moderately uncompressible ingredients, the resulting tablet composition may include from about 2 to about 6 percent of polymeric material and most preferably about 2 to about 6 percent of abrupt pressure treated excipient.

And lastly, for those difficultly compressible ingredients, examples of which include acetaminophen, ascorbic acid, pseudoephedrine, and ibuprophin, the present process offers the unexpected benefit of providing high active loading compositions including such ingredients using either direct compression or wet granulation processing. For these difficult to compress ingredients, the resulting tablet composition may include from 3 percent up to about 25 percent of polymeric material and most preferably from 3 percent up to about 10 percent of abrupt pressure treated excipient.

A preferred aspect of the present invention is the preparation of a revised compressed unit formulation excluding said first amount of excipient and including a polysaccharide material, preferably a dextrin or maltodextrin material, such as the preferred abrupt pressure treated polysaccharide material described herein, in a second amount of about 30 to about 70 percent by weight of said first amount of excipient.

A particularly preferred method substitutes an amount of abrupt treated polysaccharide material which is about 20 to about 50 percent by weight of the replaced excipient, and which exhibits the acceptable tablet properties discussed herein.

Another preferred aspect of the present invention is the production of a reduced size tablet which excludes from about 30 to about 99 percent of excipient from a commercially viable prior art tablet composition, and which exhibits the acceptable tablet properties discussed herein. A more preferred aspect of the present invention excludes a greater percentage of excipient, of about 50 to 99 percent, and most preferably about 60 to about 99 percent of excipient.

The formulations compressed in the practice of this invention and the tablet compositions of the present invention may also contain one or more additional formulation ingredients that may be selected from a wide variety of excipients known in the formulation art, in particular the pharmaceutical art. According to the desired properties of the tablet, any number of ingredients may be selected, alone or in combination, based upon their known uses in preparing tablet compositions. Such ingredients include, but are not limited to disintegrants, lubricants, flavors, flavor enhancers, sweetener, colors and preservatives. Some of these ingredients are included to aid in dissolution, consumption acceptability such as taste, texture and color of the compressed form, while others aid in the processing of the product, by improving powder flowability.

Processes for tableting are well known to those skilled in the art. Modern compression tableting techniques—irrespective of the type (and ultimate shape of the end product)—utilize a piston like device with three stages in each cycle: (1) filling—adding the powder constituents of the tablet to the compression chamber; (2) compression—forming the tablet; and (3) ejection—removing the tablet. The cycle is then repeated. Representative tablet presses are the Manesty Express 20 rotary press, and Manesty D3A Dry Cota rotary tablet press manufactured by Manesty Machines Ltd., Liverpool, England, and the Key International Rotary tablet Press manufactured by Key International, Englishtown, N.J. It will be appreciated by those skilled in the art that other tableting machines capable of compressing a tablet can also be used.

In order to make tablets, preferably all ingredients—or at least the carrier or hardening agent which typically makes up the bulk of the tablet—must have certain physical characteristics, including the ability to flow freely, and acceptable cohesion (or compressibility). Because many materials have some, or none, of these qualities, techniques must be developed to impart these characteristics to the constituents. In this context, "free flowing" means that the particles to be compressed must enter the compression chamber as discreet particles. While particles which are not "free flowing" can be used in tableting contexts, they can be utilized only if force feeders or other mechanical means are utilized to move the particles. To facilitate the free-flowing nature of the particle mixture, the ingredient mixture is typically milled or granulated prior to introduction into the tablet press. Sometimes a lubricant is added to the formulation. Such lubricants are commonly included in the final tableted product in amounts usually less than 1% by weight.

Two critical criteria in the quality of a tablet are crushing strength (or hardness) and friability. The resistance of the tablet to chipping, abrasion, or breakage under conditions of storage, transportation and handling before usage depends on its hardness. Tablets of insufficient hardness exhibit capping and/or lamination and can easily break apart or disintegrate under normal handling and packaging conditions. Tablets of insufficient hardness cannot be used for lozenges or mints which are designed to be sucked in the mouth, releasing the active ingredient(s) or flavor over time, and may have an undesirable powdery, grainy or coarse mouthfeel.

Hardness is measured by determining lateral breaking strength (expressed in kiloponds or Strong Cobb Units wherein 1 kp=1.4 S.C.U.) exerted on a single tablet at the moment of rupture. Acceptable hardness depends on the desired mouthfeel and the expected end use and packaging conditions of the tablet, but in most contexts, tablet hardness must be greater than about 7 kp to be commercially useful.

Friability is also a standard test known to one skilled in the art. Friability is measured under standardized conditions by weighing out a certain number of tablets (generally 20 or more), placing them in a rotating Plexiglas drum in which they are lifted during replicate revolutions by a radial louver, and then dropped through the diameter of the drum. After replicate revolutions, the tablets are reweighed and the percentage of powder "rubbed off" or broken pieces is calculated. Friability in the range of about 0% to 3% is considered acceptable for most drug and food tablet contexts. Friability which is about 0% to about 1% is preferred, while 0% to 0.6% is more preferred, while friability less than about 0.3% is most preferred.

Using various compression forces (0.1 to 6.0 tons), tablet hardness limits of 5.0 SCU to 11.0 SCU (7 kp to 12 kp), 10.0 SCU to 14.0 SCU (14 kp to 19 kp) and 14.0 SCU to 28.0 SCU (19 kp to 39 kp) for various types of formulations, respectively, will provide acceptable results. Typically, formulations of the present invention are compressed using about 0.75 to about 3.5 ton pressure settings. These hardnesses result in acceptable adherence of the press coat to the core tablet for all three products, with no picking, capping or lamination. When the compositions are compressed within those hardness limits, broken or chipped tablets are minimized or eliminated, and weight loss is expected to be less than one percent. Tablet thicknesses are within five percent of the average thicknesses and tablet dissolution results are well within the specification of Q=75% in 45 minutes according to the U.S. Pharmacopoeia National Formulary.

A variety of tablets may be produced by the present invention. Depending on the hardness, and palette acceptable flavoring and lubricant excipients included in the formulation, the tablet may be either chewable or swallowable.

Chewable tablets produced according to the present invention exhibit a hardness within the range of about 5 SCU to about 11 SCU (7 kp to 15 kp). A most preferred range is between about 7 to about 9 SCU (9 kp to 12 kp).

Swallowable tablets may exhibit a hardness within the range of about 10 SCU to about 28 SCU (about 14 kp to about 39 kp), with a preferred hardness between about 12 to about 35 SCU (17 kp to 35 kp).

Whether the present process produces a chewable or swallowable tablet, the tablets friability is within the range of about 0.6% to 0%, and preferably 0.3 to 0%.

Swallowable tablets made according to the present invention may be formulated to disintegrate in more than 20 seconds and in less than 30 minutes in accordance with USP Specification 701. The minimum disintegration time of 20 seconds permits the consumer sufficient time to swallow a whole tablet and avoid in-mouth dissolution. Preferred dissolution times are greater than about 40 seconds, more preferably greater than 60 seconds and most preferably more than about 90 seconds to permit the tablet to travel the esophageal channel intact. If the disintegration time is less than 30 seconds, the surface integrity of the tablet is compromised in the mouth providing the dissolution of the surface layer after a few moments residence time. Such tablets are typically coated thinly to mask the taste of the active ingredient from the consumer. It is preferred that tablets made according to this invention maintain their surface integrity for more than about 15 seconds or more to avoid the necessity for a taste masking coating. It is believed that such surface integrity properties are achieved with a disintegration time of about 40 seconds or more.

The present invention is also useful in the preparation of pellets manufactured using pressurized extrusion processes. In these processes, a wet mixture or mash is passed through an extrusion nozzle to form cylindrical pellets. This process requires that the mash maintain a flowability and cohesiveness such that it passes through the extrusion nozzles easily and maintains a cylindrical shape thereafter. Use of the present invention permits the preparation of a high active loaded extrusion mash with a minimum of solvent, whether is be aqueous or non-aqueous. The resulting pellet maintains its cohesive nature and reduces chipping and disintegration characteristic of prior art formulations.

Testing Apparatus and Methods

Tablet hardness is determined by using the Schleuniger Hardness Tester made by Dr. K. Schleuniger & Co. Another representative hardness tester is the Model HT-300 manufactured by Key International, Inc., and the Vector Corporation Tablet Hardness Tester, Model #Computest.

Tablet friability is determined by using the Roche friability method (Remington's—Pharmaceutical Sciences, Ed. 1980, page 1558—Mack Publishing Company) and a friability tester, particularly the Distek Friabilator.

Dissolution time of the active ingredient is determined for all the tablets by the method described in the USP XXII, page 683 and by using the equipment described in the USP XXII, pages 1578–9, Apparatus 1. An exemplary commercial system is the Distek Dissolution System 2100B, Model 2100B.

Disintegration time for the tablets, coated tablets and capsules prepared according to the present invention is evaluated according to the method described in the USP XXII, pages 1577–1578 (Procedure 701). An exemplary commercial system is the Distek Disintegration Tester, Model ED-2.

The invention is illustrated in the following examples. The examples do not limit the scope of the invention in any manner. All percentages and ratios are by weight unless otherwise stated.

EXAMPLES

The tablets exemplified herein are formulated and include the active ingredients, Del Tab™ excipient and small amounts of lubricant to facilitate the tablet punching operation and of croscarmellose sodium to aid in disintegration.

Example 1

This example illustrates the practice of the present invention as applied to a commercially available calcium citrate malate composition. A tablet is prepared in accordance with the following steps:

(1) 2193 g of calcium citrate malate ("CCM"), 0.37 g of Vitamin D3, 22.7 g of magnesium stearate and 69.28 g of DEL TAB excipient are dry blended in a Hobart mixer at room temperature.

(2) 200 g of distilled water are added to the dry blend and the resulting wet mixture is granulated.

(3) The granulate is sieved through a 20 mesh screen.

(4) 2244.5 g of the sieved granulate is mixed with 22.7 g of Ac-Di-Sol® (SD711)(brand of croscarmellose sodium, NF).

(5) The resulting mixture is loaded into the hopper of a Key International Rotary Tablet Press (Model DC16), equipped with a half inch concave bevel edge tooling, with the tableting pressure set at 3.5 tons and the fill depth gauge set at 15 mm.

The formulation prepared in accordance with this example is described in the chart below as a normalized formulation and is compared with the commercial formulation from which it was derived.

| Ingredient | Commercial Formulation (g) | Invention Formulation (g) | |
|---|---|---|---|
| Calcium Citrate Malate (21% Ca) | 634.92 | 634.92 | |
| Vitamin D3 500 IU/mg | 0.15 | 0.15 | |
| Dicalcium Phosphate Dihydrate | x | 0 | |
| Microcrystalline Cellulose | x | 0 | |
| Silicon Dioxide, Anhyd., FP, NF, FCC | x | 0 | |
| Stearic Acid Powder | x | 0 | |
| Corn Starch Bleached | x | 0 | |
| Croscarmellose Sodium, NF | x | x | |
| Mg Stearate | x | x | |
|  | Sum of x | 14 | |
| Del-Tab ™ excipient | 0 | 20 | 20 g of DEL TAB ™ replace 444 g of MCC, Ca2PO4 & starch. |
| Excipient Subtotal | 459 | 34 | |
| Total Tablet Weight (g) | 1094 | 669 | |
| Excipient exclusion | NA | 93% | |
| Tablet Hardness | 27 | 12.4 | |
| Active/Loading Percentage | 58% | 95% | |
| Tablet Size Reduction | NA | 39% | |

The present process is particularly effective: the tablet size is reduced by 39%, 93% of excipient is eliminated from the commercially available tablet formulation; the active to inactive ingredient ratio increased from 58% to 95%; the amount of Del Tab excipient is 3% of the total by weight; and the amount of total excipient, including lubricant and disintegrant, is only 5% by weight.

Example 2

When tablets are prepared using varying amounts of disintegrant the hardness may be modified. Example 2A–2E are prepared in substantially the same manner as Example 1 except that the following amounts of excipient: are used:

Example 2A (0% Ac-Di-Sol) (3% DelTab);
Example 2B (5% Ac-Di-Sol)(3% DelTab);
Example 2C (2% Ac-Di-Sol)(3% DelTab);
Example 2D (1% Ac-Di-Sol)(3% DelTab); and,
Example 2E (0.75% Ac-Di-Sol)(3% DelTab).

Example 3

The process of Example 1 is modified by dry mixing all the ingredients, except the Del Tab excipient, in a Hobart mixer. After the ingredients are thoroughly mixed, a 30% aqueous solution of Del Tab excipient is added followed by granulation of the wetted mixture. Using this procedure, less water (about 20% less) may be used to achieve an excellent flowable granulation for tableting. The disintegration properties of tablets produced using this mixing procedure are designated.

Examples 3A–3D include the following amounts of excipient:

Example 3A (0% Ac-Di-Sol)(3% DelTab);
Example 3B (1% Ac-Di-Sol)(3% DelTab);
Example 3C (3% Ac-Di-Sol)(3% DelTab); and,
Example 3E (5% Ac-Di-Sol)(3% DelTab).

The following formulation, as well as many others, may also be prepared with excellent results in accordance with the process of this invention. Example 4:

| Ingredient | Commercial Formulation (g) | Invention Formulation (g) | |
|---|---|---|---|
| Zinc Propionate (29% Zn) | 7.035 | 7.035 | |
| Manganese Gluconate Fine Granular | 6.764 | 6.764 | |
| Vitamin D3 500 IU/mg | 0.125 | 0.125 | |
| Copper Gluconate Powder (14% Cu) | 3.643 | 3.643 | |
| Calcium Citrate Malate (21% Ca) | 952.381 | 952.381 | |
| Dicalcium Phosphate Dihydrate Unmilled | x | 0 | |
| Microcrystalline Cellulose, Granular | x | 0 | |
| Soy Isoflavone Conc. 34% Isoflavones | x | x | |
| Croscarmellose Sodium, NF | x | x | |
| Stearic Acid | x | x | |
| Magnesium Stearate | x | x | |
|  | Sum of xs | 34.6 | |
| Del-Tab ™ excipient | 0 | 53 | 53 g of DEL TAB ™ replaces 448 g of MCC & Ca2PO4 |
| Excipient Subtotal | 430.05 | 87.6 | |
| Total Tablet Weight (g) | 1400 | 1022.95 | |
| Excipient exclusion | NA | 80% | |
| Active/Loading Percentage | 69% | 91% | |

-continued

| Ingredient | Commercial Formulation (g) | Invention Formulation (g) |
|---|---|---|
| Tablet Size Reduction | NA | 27% |

The examples described in the Tables below demonstrate the use of various commercially available starches and celluloses in addition to the abrupt pressure treated dextrin, Del Tab, for use in the practice of the present invention. Each of the formulated tablets were tested to determine their hardness, friability and disintegration times. Table 1 shows the results using tablets including calcium citrate malate. Table 2 shows results of tablets comprising dicalcium phosphate. Each formulation example included the polysaccharide material or other excipient in percentage amounts of 1%, 2% or 3% by weight.

The following legend identifies the materials used in the tested formulations:

TABLE 1

Calcium Citrate Malate Tablets

| Excipient | Wt. (mg) | Thickness (in.) | Hardness (Kp) | Dis-integration (±1 sec.) | Friability (% loss) |
|---|---|---|---|---|---|
| 1% DT-GS | 889 ± 10 | .233 | 22.0 ± 4 | 35 | 0.05 |
| 1% DT-HM | 846 ± 16 | .230 | 17.6 ± 2 | 54 | 0.03 |
| 1% DT-LM | 892 ± 13 | .230 | 35.7 ± 4 | 75 | −0.06 |
| 1% CC1500 | 896 ± 20 | .230 | 23.9 ± 6 | 43 | −0.01 |
| 1% NS1551 | 867 ± 19 | .229 | 24.3 ± 3 | 36 | 0.13 |
| 1% NZM | 853 ± 10 | .227 | 27.5 ± 4 | 64 | 0.12 |
| 1% MCC | 866 ± 12 | .228 | 23.5 ± 3 | 37 | −0.06 |
| 1% DCP | 883 ± 21 | .229 | 26.1 ± 4 | 37 | 0.01 |
| 2% DT-GS | 867 ± 10 | .231 | 19.9 ± 2 | 40 | −0.02 |
| 2% DT-HM | 896 ± 5 | .232 | 27 ± 2 | 80 | −0.10 |
| 2% DT-LM | 940 ± 14 | .234 | 36.0 ± 3 | 128 | −0.10 |
| 2% CC1500 | 907 ± 13 | .233 | 20.3 ± 2 | 39 | 0.13 |
| 2% NS1551 | 882 ± 17 | .232 | 19.9 ± 4 | 36 | −0.01 |
| 2% NZM | 841 ± 15 | .227 | 26.0 ± 4 | 50 | 0.07 |
| 2% MCC | 890 ± 10 | .230 | 32.4 ± 3 | 35 | 0.06 |
| 2% DCP | 910 ± 24 | .231 | 32.0 ± 5 | 35 | −0.06 |
| 3% DT-GS | 873 ± 14 | .234 | 21.3 ± 2 | 39 | 0.16 |
| 3% DT-HM | 892 ± 11 | .234 | 26.4 ± 3 | 70 | 0.01 |
| 3% DT-LM | 906 ± 9 | .236 | 38.7 ± 5 | 120 | −0.08 |
| 3% CC1500 | 903 ± 12 | .238 | 14.6 ± 3 | 35 | 0.09 |
| 3% NS1551 | 897 ± 4 | .232 | 24.9 ± 4 | 33 | −0.13 |
| 3% NZM | 841 ± 7 | .228 | 27.7 ± 4 | 80 | 0.12 |
| 3% MCC | 847 ± 27 | .229 | 31.9 ± 3 | 57 | −0.09 |
| 3% DCP | 914 ± 14 | .231 | 27.0 ± 2 | 32 | −0.10 |

DT-HM = DEL-TAB High Moisture (8.4%)
DT-LM = DEL-TAB Low Moisture (3.0%)
CC1500 = Colorcon 1500
NS1551 = National Starch 1551
NZM = N-Zorbit M (mixture of maltodextrin and ammonium bicarbonate sold by National Starch and Chemical Company)
MCC = Microcrystalline cellulose (Avicil)
DCP = Dicalcium phosphate (Encompress)
M051X = Emdex

TABLE 2

Dicalcium Phosphate Tablets

| | Weight (g) | Thickness (in.) | Hardness (Kp) | Dis-integration (±1 sec.) | Friability (% loss) |
|---|---|---|---|---|---|
| 1% MCC | 1.32 ± .01 | .247 | 24.5 ± 2 | 8 | 0.03 |
| 1% DT-LM | 1.36 ± .01 | .254 | 28.5 ± 2 | 22 | 0.16 |
| 1% DT-HM | 1.35 ± .01 | .249 | 25.8 ± 1 | 15 | 0.10 |
| 1% DT-GS | 1.33 ± .02 | .244 | 24.0 ± 2 | 11 | 0.31 |
| 1% NS1551 | 1.32 ± .01 | .247 | 22.2 ± 1 | 8 | 0.09 |
| 1% CC1500 | 1.33 ± .01 | .246 | 23.6 ± 2 | 9 | 0.04 |
| 1% M051X | 1.34 ± .01 | .250 | 25.6 ± 1 | 10 | 0.18 |
| 1% NZM | 1.30 ± .01 | .245 | 23.1 ± 2 | 19 | 0.20 |
| 2% MCC* | 1.28 ± .01 | .244 | 21.8 ± 1 | 8 | 0.19 |
| 2% DT-LM* | 1.33 ± .02 | .247 | 27.9 ± 2 | 43 | 0.19 |
| 2% DT-HM* | 1.32 ± .02 | .247 | 27.0 ± 2 | 29 | 0.11 |
| 2% DT-GS | 1.33 ± .02 | .253 | 21.0 ± 1 | 20 | 0.32 |
| 2% NS1551 | 1.38 ± .02 | .254 | 22.5 ± 2 | 20 | 0.12 |
| 2% CC1500 | 1.38 ± .01 | .257 | 24.4 ± 1 | 20 | 0.25 |
| 2% M051X | 1.35 ± .01 | .253 | 25.7 ± 1 | 20 | 0.05 |
| 2% NZM | 1.26 ± .02 | .254 | 20.6 ± 2 | 20 | 0.18 |
| 3% MCC | 1.30 ± .02 | .248 | 22.3 ± 3 | 8 | 0.41 |
| 3% DT-LM | 1.41 ± .03 | .261 | 36.0 ± 5 | 105 | 0.13 |
| 3% DT-LM (2nd run) | | | 28.4 | 97 | |
| 3% DT-HM | 1.37 ± .02 | .258 | 30.0 ± 1 | 39 | 0.12 |
| 3% DT-HM (2nd run) | | | 26.2 | 42 | |
| 3% DT-GS | 1.30 ± .01 | .253 | 21.4 ± 1 | 13 | 0.39 |
| 3% NS1551 | 1.34 ± .01 | .256 | 23.9 ± 1 | 6 | −0.01 |
| 3% CC1500 | 1.38 ± .02 | .258 | 26.0 ± 2 | 6 | 0.07 |
| 3% M051X | 1.36 ± .01 | .255 | 29.3 ± 2 | 10 | 0.23 |
| 3% NZM | 1.18 ± .04 | .241 | 18.2 ± 3 | 45 | 0.44 |

In addition to the active ingredient and the noted additive material, the tablet formulations described in the above tables include no more than about 1.9% of a combination of either stearic acid or magnesium stearate and either croscarmellose sodium or AcDiSol. It should further be noted that three forms of the DelTab excipient are used in these examples: DelTab LM (where the material is prepared with a moisture content less than about 3%), DelTab HM (where the moisture content is raised to about 8%), and Del Tab GS (wet granulated DelTab). All the formulations were prepared by mixing the dry ingredients together, introducing the stearic acid or stearate lubricant last and directly compressing the composition in a tablet press set at a compression force of 0.75 tons.

The data in Table I shows that the hardest tablets are prepared using DelTab LM at 1%, 2% and 3%. These tablets exhibit the longest disintegration times at all the tested concentrations, that is 75, 128 and 120 seconds respectively. At a 1% additive concentration, DelTab HM and N-Zorbit formulations exhibited disintegration times in excess of about 50 seconds (54 and 64 seconds respectively), although both tablets were not as hard (at 17 and 27 respectively), as the DelTab LM formulation tablets. The 2% and 3% DelTab LM formulated tablets retained their hardness (36 and 38 respectively), and exhibited an increase in disintegration time to about two minutes or more. Tablets including a larger percentage of DelTab HM also exhibited an increase in tablet hardness and a longer disintegration time, although there appears to be little difference between the DelTab HM 2% and 3% tablets. On the other hand, tablet formulations including percentages of N-Zorbit larger than 1% exhibited no increase in hardness and only a slightly longer disintegration time.

The test results of dicalcium phosphate tablets as described in Table 2 show the same trend for the DelTab excipients: tablet formulations including DelTab exhibit the hardest tablets with the longest disintegration times at each concentration tested. The disintegration times are uniformly short for these tablets except for the 3% DelTab formulation that disintegrates in about 100 seconds. In contrast, no other formulation withstands disintegration for more than 50 seconds, while the only other formulations which last for 40 seconds or more are the 2% DelTab and 3% N-Zorbit formulations.

Applicants have prepared acceptable tablets including polysaccharide excipient and difficult to compress materials using a processing method that involves the spray application of a solution of polysaccharide to a fluidized bed of active ingredient. As little as about 7.5% of polysaccharide excipient has been found to be required to prepare acceptable tablets. In contrast, applicants know only of prior art acetaminophen tablets comprising no less than about 27% starch excipient. Tablet compositions comprising acetaminophen and 10% total non-active excipient, were prepared as described below in Example 5.

Example 5

1500 ml of an aqueous solution of Del-Tab (50% by weight) and of polyvinylpovidone (50 gm, 6% by weight) is sprayed onto a fluidized bed containing powdered acetaminophen (9000 gm) and sodium starch glycolate (150 gm) in a Glatt Fluid Bed. The solution was maintained at a temperature of about 80 degrees C. When the spraying is complete, the temperature of the fluidized bed air is raised to about 100–125 degrees C until the moisture level of the powder making up the fluidized bed is reduced to less than about 2%.

The dried powder is mixed with 0.5% by weight of stearic acid, screened through 20 mesh and introduced into a direct compression tableting press. The tablets obtained have an acceptable hardness and friability.

The final composition of the tablet are as follows:

| 1) | Del-Tab | 7.5% |
| 2) | PVP | 0.5% |
| 3) | APAP | 90% |
| 4) | SSG | 1.5% |
| 5) | Stearic Acid | 0.5% |

PVP=Polyvinylpovidine
APAP=Acetaminophen
SSG=Sodium Starch Glycolate

Another method for the preparation of compression forms incorporating difficult-to-compress active ingredients is disclosed in related patent application Ser. No. 60/206,142, filed on the same day herewith.

We claim:

1. A process for increasing the percentage of active ingredient relative to non-active excipients in a compressible formulation, consisting essentially of the steps of:
   i) determining a formula of a compression formulation including one or more active ingredients and a first amount of one or more non-active hardening or binder excipients;
   ii) preparing a revised formulation based on said formula wherein said first amount of excipient is replaced with an abrupt pressure treated polysaccharide material in a second amount of about 1 to about 50 percent by weight of said first amount of excipient;
   iii) mixing said revised formulation to form a reduced volume mixture; and
   iv) compressing said reduced volume mixture to form a composition wherein at least about 90% by weight of the composition is said active ingredient.

2. A process according to claim 1 wherein said reduced volume mixture is formed into a tablet or pellet.

3. A process according to claim 2 wherein said pellet is extruded.

4. A process according to claim 2 wherein said tablet or pellet comprises a food, a nutritional supplement or a pharmaceutical suitable for animal or human ingestion.

5. A tablet or pellet manufactured according to the method of claim 2.

6. A process according to claim 1 wherein said excipient is selected from the group consisting of silica, cellulose, microcrystalline cellulose, calcium carbonate, mono-, di- or tri-calcium phosphate, spray-dried lactose, anhydrous lactose, dicalcium phosphate dihydrate, unmilled, spray-congealed mannitol, ungelatinized starch, and partially or fully pregelatinized starch.

7. A process according to claim 1 wherein said mixture is wet granulated prior to compression.

8. A process according to claim 6 wherein said excipient comprises microcrystalline cellulose.

9. A process according to claim 4 wherein said tablet is a chewable tablet.

10. A process according to claim 4 wherein said tablet is a swallowable tablet.

11. A process according to claim 10 wherein said tablet disintegrates in less than 30 minutes in accordance with the test conditions of USP Specification 701.

12. A process according to claim 11 wherein said tablet disintegrates in more than about 20 seconds.

13. A process according to claim 12 wherein said tablet disintegrates in more than about 40 seconds.

14. A process according to claim 12, wherein said polysaccharide material is selected from the group consisting of dextrin and maltodextrin materials.

15. A process according to claim 14 wherein said dextrin material comprises an abrupt pressure treated polysaccharide material.

16. A process according to claim 15 wherein said active ingredient is a difficult to compress material and said dextrin material comprises an abrupt-pressure treated starches.

17. A process according to claim 9 wherein said chewable tablet hardness is within the range of about 7 kp to about 15 kp.

18. A process according to claim 12 wherein said swallowable tablet hardness is within the range of about 14 kp to about 39 kp.

19. A process according to claim 4 wherein said tablet or pellet has a friability of about 0% to about 0.6%.

20. A process according to claim 2, wherein said active ingredient is easily compressible.

21. A process according to claim 2, wherein said active ingredient is moderately compressible.

22. A process according to claim 2, wherein said active ingredient is moderately uncompressible.

23. A process according to claim 19 wherein said mixture is compressed using a pressure setting of about 1 to about 3.5 ton.

24. A process according to claim 20 wherein said mixture is compressed using a pressure setting of about 1 to about 3.5 ton.

25. A process according to claim 21 wherein said mixture is compressed using a pressure setting of about 1 to about 3.5 ton.

26. A process according to claim 19 wherein said mixture includes from about 1 to about 4 percent of abrupt pressure treated material.

27. A process according to claim 20 wherein said mixture includes from about 2 to about 6 percent of abrupt pressure treated material.

28. A process according to claim 21 wherein said mixture includes from about 4 to about 25 percent of abrupt pressure treated material.

29. A process according to claim 1 wherein the ratio of active ingredients to polysaccharide material is from about 9:1 to about 9.9:1.

* * * * *